(12) United States Patent
Groves

(10) Patent No.: US 11,998,668 B2
(45) Date of Patent: Jun. 4, 2024

(54) WORKPIECE RETENTION MECHANISM FOR ORAL CARE DEVICE

(71) Applicant: KONINKLIJKE PHILIPS N.V., Eindhoven (NL)

(72) Inventor: Jeffrey Groves, Seattle, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 618 days.

(21) Appl. No.: 17/261,896

(22) PCT Filed: Jul. 23, 2019

(86) PCT No.: PCT/EP2019/069837
§ 371 (c)(1),
(2) Date: Jan. 21, 2021

(87) PCT Pub. No.: WO2020/020907
PCT Pub. Date: Jan. 30, 2020

(65) Prior Publication Data
US 2021/0283327 A1    Sep. 16, 2021

Related U.S. Application Data

(60) Provisional application No. 62/702,446, filed on Jul. 24, 2018.

(51) Int. Cl.
*A61C 17/22* (2006.01)
*A61C 17/02* (2006.01)
*A61M 3/02* (2006.01)

(52) U.S. Cl.
CPC ....... *A61M 3/0279* (2013.01); *A61C 17/0202* (2013.01)

(58) Field of Classification Search
CPC ... F16L 37/0847; F16L 37/096; F16L 37/098; F16L 37/0985; F16L 37/121;
(Continued)

(56) References Cited

U.S. PATENT DOCUMENTS 3,872,714 A    3/1975 Carlson, Jr.
6,199,920 B1 *  3/2001 Neustadtl ............ F16L 37/0985
                                                    285/903
(Continued)

FOREIGN PATENT DOCUMENTS

CN        1492747 A      4/2004
CN      106562831 A      4/2017
(Continued)

OTHER PUBLICATIONS

International Search Report and Written Opinion, International Application No. PCT/EP2019/069837, dated Oct. 15, 2019.

*Primary Examiner* — Aaron M Dunwoody

(57) ABSTRACT

A connection mechanism (18) for connecting a workpiece (12) to a handle assembly (14) of an oral care device (10). A collet (30) has an axially extending beam (32) and a radially extending protrusion (34). The protrusion has a latching surface (44) that prevents disengagement of the workpiece from the handle assembly when in a locked configuration. A cam feature (40) is configured to convert an axial force exerted on the collet into radial deflection of the beam to transition the connection mechanism to an unlocked configuration in which the latching surface is disengaged from the corresponding surface of the workpiece. The beam is configured to return to the default position after the axial force is released due to strain energy in the beam resulting from the radial deflection.

5 Claims, 4 Drawing Sheets

FIG. 5

(58) Field of Classification Search
CPC ..... F16L 37/122; F16L 37/127; F16L 37/133; F16L 37/138; F16L 37/53; A61C 17/222; A61C 17/02; A61C 17/022; A61C 17/024; A61C 17/028; A61C 17/227; A61C 17/00; A61C 17/0202
See application file for complete search history.

(56) References Cited

U.S. PATENT DOCUMENTS

| | | |
|---|---|---|
| 2004/0016067 A1 | 1/2004 | Kraemer |
| 2010/0043156 A1 | 2/2010 | Kressner |
| 2012/0017710 A1 | 1/2012 | Kramp |
| 2014/0150190 A1 | 6/2014 | Fattori |
| 2014/0341636 A1 | 11/2014 | Fattori |
| 2015/0020325 A1 | 1/2015 | Yoshida |
| 2015/0060578 A1* | 3/2015 | Prociw ................ F16L 37/0982 239/600 |
| 2015/0209125 A1 | 7/2015 | Fattori |
| 2017/0042638 A1 | 2/2017 | Lee |

FOREIGN PATENT DOCUMENTS

| | | |
|---|---|---|
| CN | 106667606 A | 5/2017 |
| EP | 100205 A2 | 2/1984 |
| EP | 756127 A1 | 1/1997 |
| GB | 1331003 | 9/1973 |
| WO | 2000037017 A1 | 6/2000 |

\* cited by examiner

WORKPIECE RETENTION MECHANISM FOR ORAL CARE DEVICE

This application is the U.S. National Phase application under 35 U.S.C. § 371 of International Application No. PCT/EP2019/069837, filed on 23 Jul. 2019, which claims the benefit of U.S. Provisional Application No. 62/702,446, filed 24 Jul. 2018. These applications are hereby incorporated by reference herein.

FIELD OF THE INVENTION

The present disclosure is directed generally to oral care devices and more particularly to mechanisms for securing together components of oral care devices.

BACKGROUND

Oral care devices such as oral irrigators and fluid-based flossing devices can be used to improve oral health care. Some oral irrigators feature a removable workpiece or nozzle component that is secured to a handle while in use but can be detached and replaced when desired by the user. The workpiece component may be unlocked from the handle via user manipulation of a corresponding securing mechanism. For example, the securing mechanism may include a threaded outer diameter ring that is part of the handle assembly and a threaded interior locking feature located on the workpiece. However, existing securing mechanisms require additional moving parts, and must be manipulated by the user during both insertion and removal of the workpiece component.

Accordingly, there is a continued need in the art for additional connection mechanisms that provide cost effective solutions for components of oral care devices that do not leak during operation of the device, which may use fluid when operating, especially for use in oral care devices that have replaceable or interchangeable workpieces.

SUMMARY OF THE INVENTION

The present disclosure is directed to inventive connection mechanisms for oral care devices. The mechanism includes a first component having a male interface or insert and a second component having a female interface or socket. The first and second components can include a workpiece and/or nozzle component and a handle assembly of an oral care device, such as an oral irrigator or fluid-based flossing device. Connection of the male and female interfaces can detachably lock the first and second components together. The connection mechanism can include a collet having one or more axially extending fingers or beams having radially extending projections. Advantageously, the strain energy of the material of the collet can be used to generate a spring force that enables the protrusions to repeatedly transition between a locked configuration in which the protrusions are relatively radially inwardly positioned and an unlocked position in which the protrusions are relatively radially outwardly positioned. When radially outwardly positioned, a latching surface of the protrusions is disengaged from the male interface, which enables the male interface to be disconnected from the female interface. The spring force generated by the strain energy can also be used to enable the protrusions to shift radially outwardly to permit the male interface to be inserted and then to resiliently move back radially inwardly into engagement with one or more corresponding detents of the male interface. Advantageously, this provides a compact mechanism that contains few parts and that does not require user manipulation of the collet while forming the connection between the male and female interfaces.

A connection mechanism for an oral care device, including a handle assembly configured to receive a workpiece; a fluid pathway formed axially from the handle assembly through the workpiece when connected; a collet having an axially extending beam and a protrusion extending radially from the beam; a latching surface on the protrusion configured to prevent the workpiece from being withdrawn from the handle assembly in a first axial direction when the connection mechanism is in a locked configuration in which the latching surface is engaged with a corresponding surface of the workpiece; and a cam feature configured to convert an axial force exerted on the collet in a second axial direction, opposite to the first axial direction, into radial deflection of the beam from a default configuration to transition the connection mechanism to an unlocked configuration in which the latching surface is disengaged from the corresponding surface of the workpiece; wherein the beam is configured to return to the default position after the axial force is released due to strain energy in the beam resulting from the radial deflection.

In one embodiment, the protrusion includes a receiving surface axially opposite from the latching surface that is configured to receive the workpiece during insertion of the workpiece in the second axial direction. In one embodiment, the beam is configured to deflect radially in response to increased engagement of the workpiece against the receiving surface to transition the connection mechanism to the locked configuration when the latching surface is axially aligned with the corresponding surface of the workpiece at which the strain energy returns the beam to its default configuration.

In one embodiment, the beam is configured to deflect radially in response to the workpiece regardless of whether the axial force is applied to the collet. In one embodiment, the corresponding surface is defined by a detent of the workpiece. In one embodiment, the beam is arranged radially external to the handle assembly and the handle assembly includes an opening through which the protrusion extends radially inwardly.

In one embodiment, the connection mechanism further includes a collar configured to receive the axial force from a user of the oral care device and to transfer the axial force to the collet. In one embodiment, the cam feature includes a flared or angled surface engagable with an axial end of the collet. In one embodiment, the protrusion is configured to be received in a detent of the workpiece.

Generally, in another aspect, an oral care device is provided that includes a workpiece having a fluid workpiece connected to a handle assembly via a connection mechanism according to embodiments disclosed herein.

Generally, in another aspect, a connection mechanism for an oral care device is provided. The connection mechanism includes a workpiece; a handle assembly configured to receive the workpiece; a fluid pathway formed axially from the handle assembly through the workpiece when connected; a collet having a plurality of axially extending beams arranged radially external to the handle assembly, each beam having a protrusion extending therefrom through an opening in the handle assembly to a position radially inward of an inner surface of the handle assembly when in a default configuration; a latching surface on each protrusion configured to prevent the workpiece from being withdrawn from the handle assembly in a first axial direction when the connection mechanism is in a locked configuration in which the latching surface is engaged with a detent of the workpiece; a receiving surface on each protrusion axially opposite from the latching surface that is configured to receive a leading edge of the workpiece during insertion of the workpiece in a second axial direction opposite to the first axial direction; a collar arranged radially about the collet and configured to transfer an axial force exerted from a user of the oral care device in the second axial direction to the collet; and an angled surface of the handle assembly bordering the opening that is engageable with an axial end of the collet and configured to convert the axial force exerted on the collet into radially outward deflection of the beams to transition the connection mechanism to an unlocked configuration in which the protrusions are positioned radially outward from the detent and the latching surfaces are disengaged from the workpiece; wherein the beams are configured to return to the default configuration after the axial force is released due to strain energy in the beams resulting from the radially outward deflection.

Generally, in one aspect, a method of connecting a workpiece and a handle assembly of an oral care device together with a connection mechanism is provided. The method includes inserting a workpiece into a handle assembly in a first axial direction; engaging a latching surface of a protrusion extending radially from an axially extending beam of a collet of the connection mechanism with a corresponding surface of the workpiece when the connection mechanism is in a locked configuration; exerting an axial force on the collet in the first axial direction; engaging an axial end of the beam against an angled surface of the handle assembly; converting the axial force into a radial deflection of the beam from a default configuration of the beam via the angled surface; disengaging the latching surface from the workpiece as a result of the radial deflection; removing the workpiece from the handle assembly after the disengaging; and returning the beam to the default configuration due to strain energy in the beam resulting from the radial deflection.

In one embodiment, the method further includes, before engaging the latching surface with the protrusion: engaging a leading edge of the workpiece with a receiving surface of the protrusion, axially opposite from the latching surface; deflecting the beam of the collet radially from the default configuration in response to engaging the leading edge with the receiving surface; aligning a detent in the workpiece axially with the protrusion; and returning the beam to the default configuration due to strain energy in the beam resulting from radially deflecting the beam when the detent is aligned with the protrusion.

In one embodiment, deflecting the beam of the collet radially from the default configuration in response to engaging the leading edge with the receiving edge occurs regardless of whether the axial force is exerted on the collet.

In one embodiment, exerting the axial force includes exerting the axial force on a collar and transferring the axial force from the collar to the collet.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION OF EMBODIMENTS

The present disclosure describes various embodiments of a connection mechanism for an oral care device. More generally, Applicant has recognized and appreciated that it would be beneficial to provide a connection mechanism having a collet that relies on strain energy of the material of the collet to transition between locked and unlocked configurations. A particular goal of utilization of certain embodiments of the present disclosure is to provide a connection mechanism that can be cost-effectively manufactured, contains few components, and does not require manual user manipulation of the mechanism to create a connection between two components with the mechanism.

In view of the foregoing, various embodiments and implementations are directed to a connection mechanism for an oral care device. The mechanism includes a first component having a male interface or insert and a second component having a female interface or socket. The first and second components can include a workpiece and/or workpiece component and a handle assembly of an oral care device, such as an oral irrigator or fluid-based flossing device. Connection of the male and female interfaces can detachably lock the first and second components together. The connection mechanism can include a collet having one or more axially extending fingers or beams having radially extending projections. Advantageously, the strain energy of the material of the collet can be used to generate a spring force that enables the protrusions to repeatedly transition between a locked configuration in which the protrusions are relatively radially inwardly positioned and an unlocked position in which the protrusions are relatively radially outwardly positioned. When radially outwardly positioned, a latching surface of the protrusions is disengaged from the male interface, which enables the male interface to be disconnected from the female interface. The spring force generated by the strain energy can also be used to enable the protrusions to shift radially outwardly to permit the male interface to be inserted and then to resiliently move back radially inwardly into engagement with one or more corresponding detents of the male interface. Advantageously, this provides a compact mechanism that contains few parts and that does not require user manipulation of the collet while forming the connection between the male and female interfaces.

Figure 1:
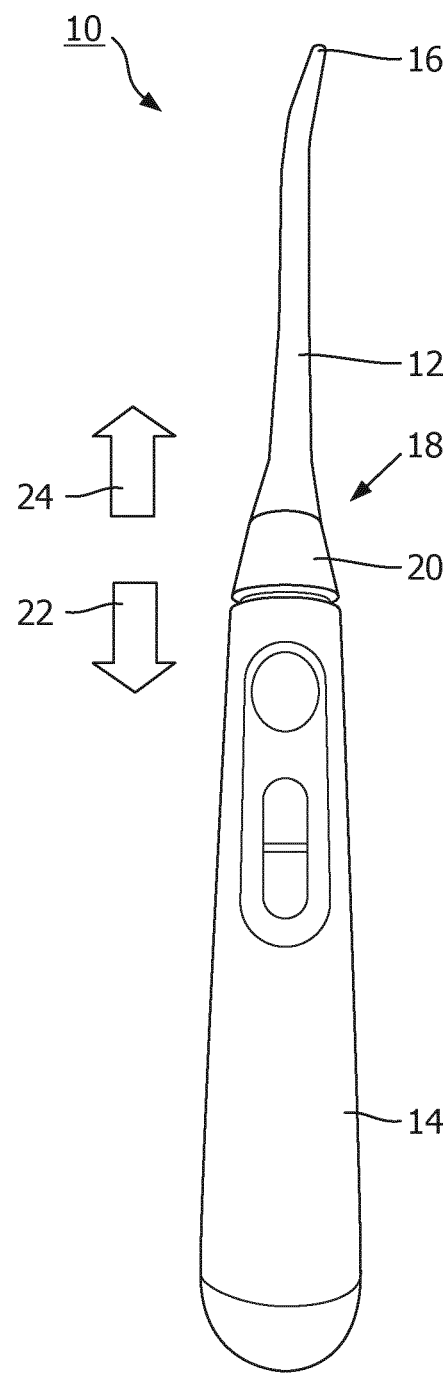
FIG. 1 is a front view of an oral care device having a workpiece connected to a handle assembly by a connection mechanism according to one embodiment disclosed herein.

Referring to FIG. 1, in one embodiment, an oral care device 10 is provided with an attachable workpiece 12 and a handle assembly 14. The oral care device 10 may be an oral irrigator, a flossing device, an electric toothbrush, or other oral care device. The attachable workpiece 12 may be a component arranged for providing an oral care function when the oral care device is operated by a user, such as a nozzle, a toothbrush head, a flosser, a multi-purpose component, or other oral care component. For example, in FIG. 1, the attachable workpiece 12 is a nozzle extending from the handle assembly 14 and arranged to deliver fluid (e.g., water, mouthwash, etc.), and/or a mix of fluid and gas, from a fluid reservoir (not shown) in the handle assembly 14 of the oral care device 10 through a fluid pathway 29 (see FIG. 2) in the workpiece via an exit 16 from the workpiece, to assist a user in performance of an oral care routine, such as interdental cleaning. The handle assembly 14 may correspondingly include components for enabling and/or controlling operation of the oral care device 10, such as a processor, memory, wireless communication module, motor, pump, gearing, battery, fluid reservoir, fluid conduits, etc.

According to embodiments disclosed herein, the oral care device 10 includes a connection mechanism 18 that enables the workpiece 12 to be removably, releasably, or detachably connected from the handle assembly 14. The connection mechanism 18 includes a collar 20 or other externally located element configured to be manipulated by a user to facilitate connection or disconnection of the workpiece 12 from the handle assembly 14. For example, as discussed in more detail below, applying a force 22 on the collar 20 in the indicated direction will transition the mechanism 18 to an unlocked state or configuration in which application of a force 24 on the workpiece 12 in the opposite direction, as indicated, causes the workpiece 12 to be disconnected from the handle assembly 14. As also discussed in more detail below, the connection mechanism 18 is configured to enable the workpiece 12 and the handle assembly 14 to form a connection when brought together, without the need to manipulate the collar 20 by means such as aligning threads, grooves, etc. and securing.

Figure 2:
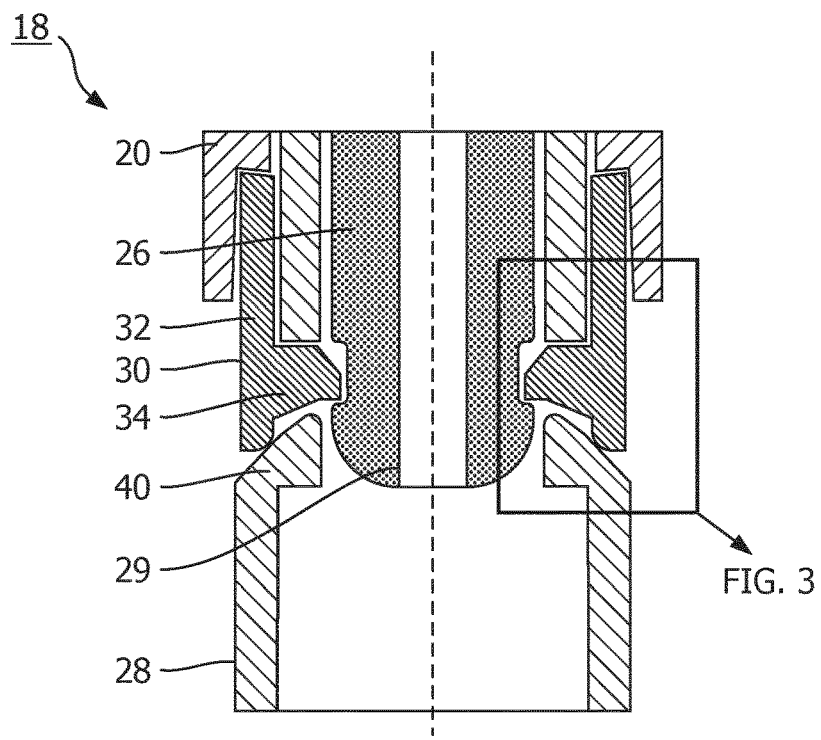
FIG. 2 is a cross-sectional view of a connection mechanism in a locked configuration according to one embodiment disclosed herein.
Figure 3:
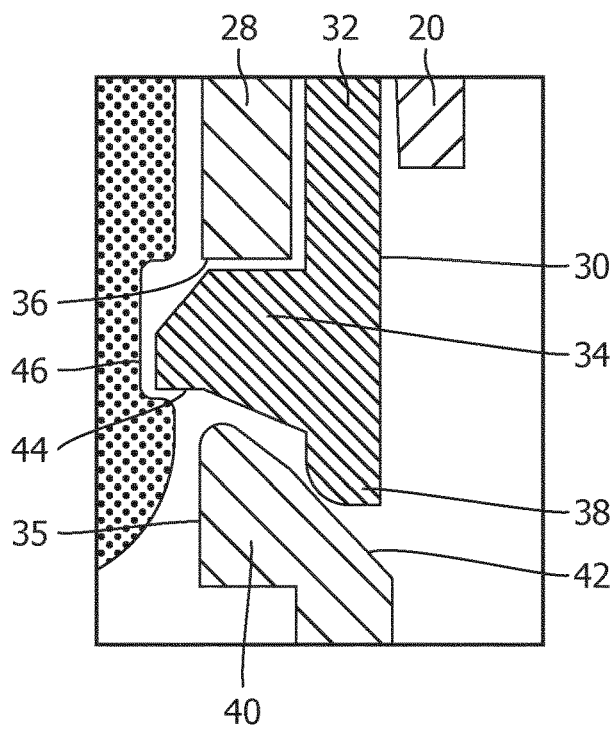
FIG. 3 is an enlarged view of the indicated portion of FIG. 2.

A cross-sectional view of the mechanism 18 in a locked configuration is shown in FIG. 2, a portion of which is enlarged in FIG. 3. As noted above, the mechanism 18 is configured to create a releasable connection between the workpiece 12 and the handle assembly 14. More specifically, the mechanism 18 of the workpiece 12 and the handle assembly 14 together comprise a male component or insert 26 and a female component or socket 28. For example, the workpiece 12 may include the insert 26, while a housing of the handle assembly 14 includes the socket 28, or vice versa. The insert 26 and socket 28 may include a fluid pathway 29 formed therethrough, e.g., enabling a fluid connection from a fluid reservoir in the handle assembly 14 to the workpiece 12 when the workpiece 12 is connected to the handle assembly 14 via the mechanism 18. Although not illustrated, it is to be appreciated that a seal (e.g., o-ring) may be included between the insert 26 and the socket 28 to provide a fluid tight connection.

The mechanism 18 also includes the collar 20, e.g., as noted with respect to in FIG. 1, and a collet 30. The collet 30 includes one or more fingers or beams 32 with latching geometry arranged annularly around the socket 28. For example, in the illustrated embodiment, each of the beams 32 is radially external to the socket 28 and includes a latching component formed as a protrusion 34 that extends radially inwardly though a corresponding slot or opening 36 in the socket 28. In this way, the protrusions 34 are provided with access to a radially internal area of the socket 28 through which the insert 26 is inserted, i.e., the protrusions 34 extending radially inward of an inner surface 35 of the socket 28. The collet 30 also includes an axial end 38 that is configured to engage against a cam feature 40 of the socket 28, which borders the opening 36. In the illustrated embodiment, the cam feature 40 includes a portion of the socket 28 that is formed as a ramp and/or includes an angled or flared surface 42. The end of the beams 32 opposite to the axial ends 38 may be joined together by a common component, such as a ring encircling the socket 28, which, in addition to the protrusions 34 in the openings 36, secures the collet 30 with respect to the socket 28.

In the locked configuration of FIGS. 2-3, a latching surface 44 of the protrusion 34 is engaged against a corresponding lip or surface of the insert 26, such as formed by a detent 46 formed in the insert 26 (e.g., individual detents or a circumferential groove). In this way, the protrusions 34 grip, grab, hold, or otherwise engage with and/or against the insert 26, thereby preventing the insert 26 from being axially withdrawn from connection with the socket 28. In other words, the workpiece 12 and the handle assembly 14 are locked together by the mechanism 18 when it is in its locked configuration. Instead of the detent 46, it is to be appreciated that the insert 26 may alternatively be arranged with a lip, flange, bulge, protrusion, etc., having a corresponding latching surface for engagement with the latching surfaces 44 of the protrusions 34.

Figure 4:
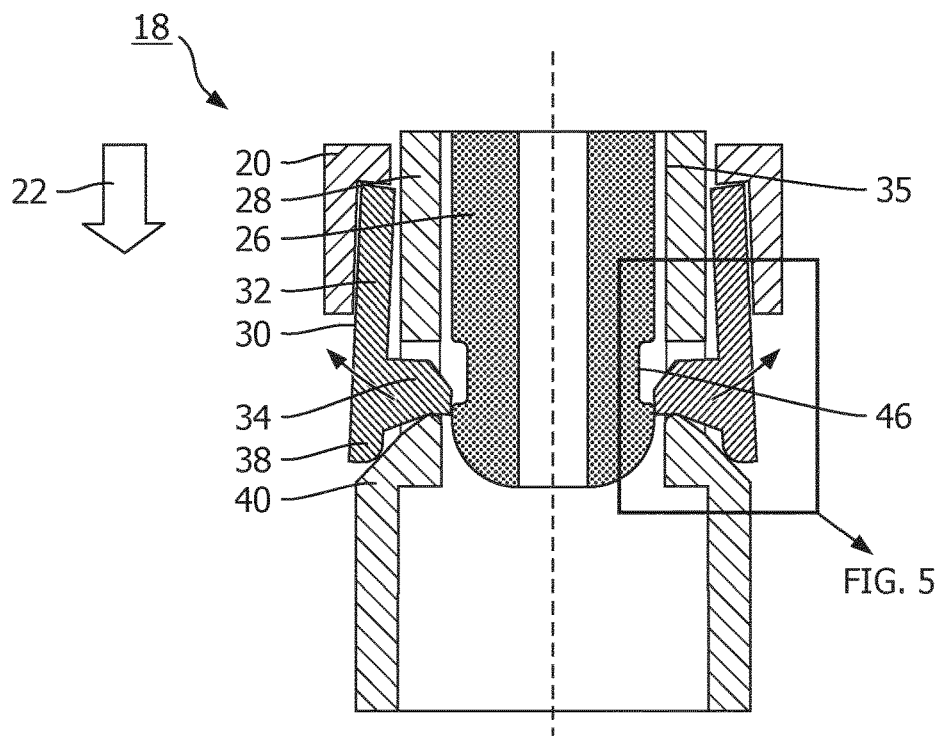
FIG. 4 is a cross-sectional view of the connection mechanism of FIG. 2 in an unlocked configuration.
Figure 5:
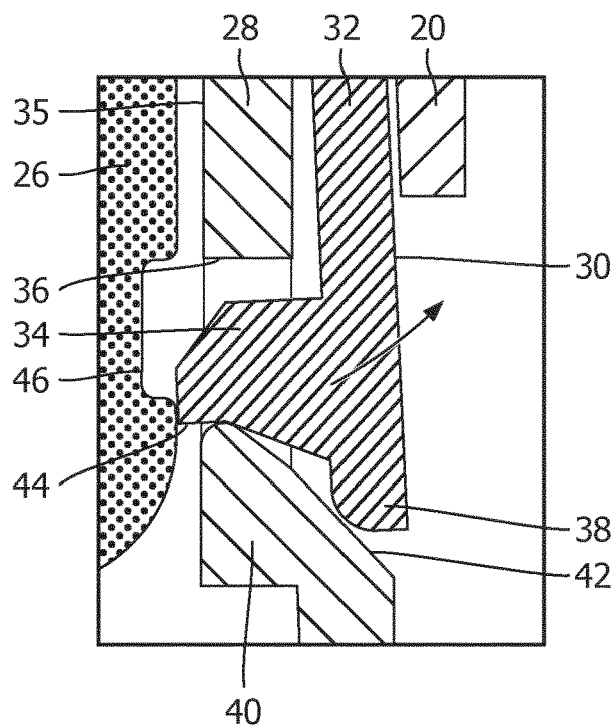
FIG. 5 is an enlarged view of the indicated portion of FIG. 4.

The mechanism 18 in an unlocked state is illustrated in FIG. 4, a portion of which is enlarged in FIG. 5. It can be appreciated that the collet 30 and the cam feature 40 are arranged such that when an axially directed force is exerted on the collet 30 (e.g., the force 22, which may be exerted directly on the collet 30 and/or via the user manipulating the collar 20), the beams 32 of the collet 30 deflect radially outwards as the axial end 38 rides along the flared surface 42. In other words, the interaction of the axial end 38 of the collet 30 with the flared surface 42 of the cam feature 40 translates or converts an axial force on the collet 30 (e.g., via the collar 20) into a radial movement of the protrusions 34.

Figure 6:
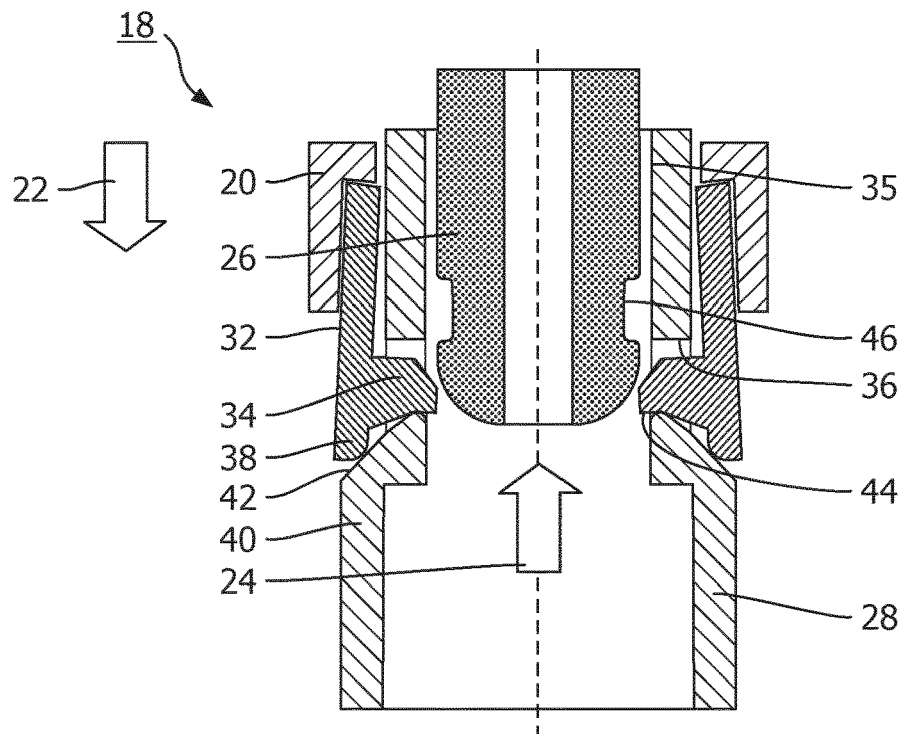
FIG. 6 is a cross-sectional view of the connection mechanism of FIG. 2 in an unlocked configuration and with an insert component disengaged from a socket component.

The opening 36 is larger than the protrusion 34 in the axial direction to simultaneously enable some degree of relative axial movement of the protrusions 34 with respect to the socket 28 as the beams 32 are radially outwardly deflected. As best shown in FIG. 5, the radially outward deflection of the beams 32 disengages the latching surface 44 of the protrusions from the corresponding surface of the insert 26, e.g., the detent 46. Once released, the insert 26 can be removed or withdrawn from engagement with the socket 28, and the workpiece 12 and the handle assembly 14 can be separated. This can be achieved by pulling the insert 26 away from the socket 28 in the direction of the force 24 as shown in FIG. 6, and also shown in and discussed with respect to FIG. 1. The outward radial deflection of the beams 32 and axial movement of the protrusions 34 may be limited by the latching surface 44 bottoming out against the leading edge of the cam feature 40.

Figure 7:
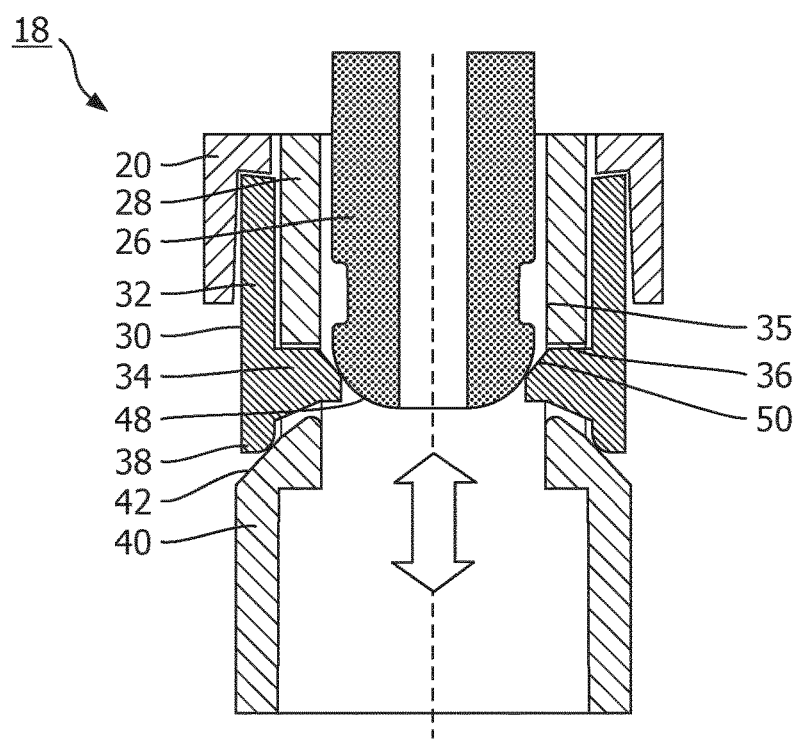
FIG. 7 is a cross-sectional view of the connection mechanism of FIG. 2 with a leading edge of an insert component engaging against a corresponding surface of a collet to initiate connection between the insert and the collet.

The deflection of the beams 32 can be maintained for as long as the user continues to exert the force 22 on the collet 30, e.g., via the collar 20. The collet 30 can be constructed from a relatively hard, resilient material, such as a metal, or a semi-crystalline plastic such as polypropylene. In this way, the strain energy of the material can provide a spring force on the beams 32 in the radially inward direction to return the collet 30 to its original or default configuration when the force 22 is released. For example, FIG. 7 shows the collet 30 returned to its natural configuration after the insert 26 has been pulled out of engagement with the protrusions 34. It is to be appreciated that the value for the force 22 required to move the collet 30 from its locked to unlocked configuration can be varied by altering the material or material properties of the collet 30, the length of the individual beams 32, the thickness/width of the individual beams 32, the angle of the flared surface 42, etc.

With reference again to FIG. 7, it is to be appreciated that external manipulation of the collar 20 or the collet 30 is not required to lock the insert 26 in the socket 28. For example, when initially installing the workpiece 12 or when replacing one workpiece for another workpiece, the insert 26 can be inserted into the socket 28 until a leading edge 48 of the insert 26 engages against a receiving surface 50 of the protrusions 34 (axially opposite to the latching surface 44). In this way, continued force on the insert 26 will cause the beams 32 to deflect radially outward similar to the above, but due to the receiving surfaces 50 sliding along the leading edge 48 of the insert 26. When the insert 26 is inserted deep enough into the socket to align the protrusions 34 axially with the detent 46, the resiliency of the material of the collet 30 will springingly return the beams 32 and the protrusions 34 back to the default configuration of the collet 30, which corresponds to the locked configuration of the mechanism 18, such as shown in FIG. 2. Similar to that described above, it is to be appreciated that the value for the force required to stab the insert 26 into the socket 28 can be set by altering the material or material properties of the collet 30, the length of the individual beams 32, the thickness/width of the individual beams 32, the angle of the leading edge 48 and/or the receiving surface 50, etc.

As shown in FIGS. 2-3, insertion of the insert 26 until the protrusions 34 are aligned with the detent 46 will cause the above-discussed engagement of the latching surface 44 with the corresponding surface of the insert 26 formed by the detent 46, thereby axially locking the workpiece 12 and the handle assembly together via engagement of the insert 26 and socket 28. Thus, the mechanism 18 as described herein advantageously minimizes the number of parts required to enable a quick-acting coupling or connection that occupies a small volume and requires few parts, and thus can be cost-effectively utilized by replaceable or disposable components such as the workpiece 12 of the oral care device 10.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. As used herein in the specification and in the claims, "or" should be understood to have the same meaning as "and/or" as defined above.

It should also be understood that, unless clearly indicated to the contrary, in any methods claimed herein that include more than one step or act, the order of the steps or acts of the method is not necessarily limited to the order in which the steps or acts of the method are recited.

The invention claimed is:

1. An oral care device, comprising:
a workpiece;
a handle assembly configured to receive the workpiece;
a fluid pathway formed axially from the handle assembly through the workpiece when connected;
a connection mechanism comprising:
a collet having a plurality of axially extending beams arranged radially external to the handle assembly, each beam having a respective protrusion extending therefrom through an opening in the handle assembly to a position radially inward of an inner surface of the handle assembly when in a default configuration;
a latching surface on each protrusion configured to prevent the workpiece from being withdrawn from the handle assembly in a first axial direction when the connection mechanism is in a locked configuration in which the latching surface is engaged with a detent of the workpiece;
a receiving surface on each protrusion axially opposite from the latching surface that is configured to receive a leading edge of the workpiece during insertion of the workpiece in a second axial direction opposite to the first axial direction;
a collar arranged radially about the collet and configured to transfer an axial force exerted from a user of the oral care device in the second axial direction to the collet; and
an angled surface of the handle assembly bordering the opening that is engageable with an axial end of the collet and configured to convert the axial force exerted on the collet into radially outward deflection of the beams to transition the connection mechanism to an unlocked configuration in which the protrusions are positioned radially outward from the detent and the latching surfaces are disengaged from the workpiece;

wherein the beams are configured to return to the default configuration after the axial force is released due to strain energy in the beams resulting from the radially outward deflection.

2. A method of connecting a workpiece and a handle assembly of an oral care device together with a connection mechanism, comprising:
- inserting the workpiece into the handle assembly in a first axial direction;
- engaging a latching surface of a protrusion extending radially from an axially extending beam of a collet of the connection mechanism with a corresponding surface of the workpiece when the connection mechanism is in a locked configuration;
- exerting an axial force on the collet in the first axial direction;
- engaging an axial end of the beam against an angled surface of the handle assembly;
- converting the axial force into a radial deflection of the beam from a default configuration of the beam via the angled surface;
- disengaging the latching surface from the workpiece as a result of the radial deflection;
- removing the workpiece from the handle assembly after the disengaging; and
- returning the beam to the default configuration due to strain energy in the beam resulting from the radial deflection.

3. The method of claim 2, further comprising, before engaging the latching surface with the protrusion: engaging a leading edge of the workpiece with a receiving surface of the protrusion, axially opposite from the latching surface; deflecting the beam of the collet radially from the default configuration in response to engaging the leading edge with the receiving surface; aligning a detent in the workpiece axially with the protrusion; and returning the beam to the default configuration due to strain energy in the beam resulting from radially deflecting the beam when the detent is aligned with the protrusion.

4. The method of claim 3, wherein deflecting the beam of the collet radially from the default configuration in response to engaging the leading edge with the receiving edge occurs regardless of whether the axial force is exerted on the collet.

5. The method of claim 3, wherein exerting the axial force includes exerting the axial force on a collar and transferring the axial force from the collar to the collet.

* * * * *